United States Patent
Panzner et al.

(10) Patent No.: US 7,858,117 B2
(45) Date of Patent: *Dec. 28, 2010

(54) AMPHOTERIC LIPOSOMES AND THEIR USE

(75) Inventors: Steffen Panzner, Halle (DE); Stefan Fankhaenel, Borsdorf (DE); Frank Essler, Mainz (DE); Cornelia Panzner, Halle (DE); Gerold Endert, Halle (DE)

(73) Assignee: Novosom AG, Halle (DE)

( * ) Notice: Subject to any disclaimer, the term of this patent is extended or adjusted under 35 U.S.C. 154(b) by 865 days.

This patent is subject to a terminal disclaimer.

(21) Appl. No.: 11/745,003

(22) Filed: May 7, 2007

(65) Prior Publication Data

US 2008/0031937 A1 Feb. 7, 2008

Related U.S. Application Data

(63) Continuation-in-part of application No. 10/081,617, filed on Feb. 21, 2002, now Pat. No. 7,371,404.

(51) Int. Cl.
   *A61K 9/127* (2006.01)
(52) U.S. Cl. ...................................... 424/450
(58) Field of Classification Search ................... 424/450
    See application file for complete search history.

(56) References Cited

U.S. PATENT DOCUMENTS

| | | | |
|---|---|---|---|
| 4,599,227 A | 7/1986 | Dees et al. | |
| 4,891,208 A | 1/1990 | Janoff et al. | |
| 5,165,994 A | 11/1992 | Kaier et al. | |
| 5,283,122 A | 2/1994 | Huang et al. | |
| 5,290,563 A | 3/1994 | Millet-Genin et al. | |
| 5,296,231 A | 3/1994 | Yarosh | |
| 5,302,389 A | 4/1994 | Kripke et al. | |
| 5,753,263 A | 5/1998 | Lishko et al. | 424/450 |
| 5,962,015 A | 10/1999 | Delrieu et al. | |
| 6,258,792 B1 | 7/2001 | Deshmukh et al. | 514/44 R |
| 6,379,698 B1 | 4/2002 | Leamon | 424/450 |
| 6,534,484 B1 | 3/2003 | Wheeler et al. | 514/44 R |
| 7,371,404 B2 | 5/2008 | Panzner et al. | |
| 7,384,923 B2 | 6/2008 | Gregoriadis | 514/44 R |
| 2007/0252295 A1 | 11/2007 | Panzner et al. | 264/4.1 |
| 2007/0269504 A1 | 11/2007 | Panzner et al. | 424/450 |

FOREIGN PATENT DOCUMENTS

| | | |
|---|---|---|
| EP | 0169812 A1 | 1/1986 |
| WO | WO-9739019 A1 | 10/1997 |
| WO | WO 00/28972 | 5/2000 |

(Continued)

OTHER PUBLICATIONS

Abstract of Japanese Patent Application No. 02-331417 (In English), Filed Nov. 29, 1990.

(Continued)

*Primary Examiner*—Gollamudi S Kishore
(74) *Attorney, Agent, or Firm*—Ivor R. Elrifi, Esq.; Mintz Levin Cohn Ferris Glovsky and Popeo PC

(57) ABSTRACT

Amphoteric liposomes are proposed, which comprise positive and negative membrane-based or membrane-forming charge carriers as well as the use of these liposomes.

24 Claims, 4 Drawing Sheets

FOREIGN PATENT DOCUMENTS

| | | |
|---|---|---|
| WO | WO-0028972 A2 | 5/2000 |
| WO | WO-0059474 A1 | 10/2000 |
| WO | WO 01/64330 | 9/2001 |
| WO | WO-0164330 A1 | 9/2001 |

OTHER PUBLICATIONS

Budker et al., "pH-sensitive, cationic liposomes: a new synthetic virus-like vector", *Nat. Biotechnol.*, 14(6)760-64 (1996).

Chu et al., "pH-Sensitive Liposomes", *J. Liposome Res.*, 4(1)361-395 (1994).

Couvreur et al., "pH-Sensitive Lipsomes: An Intelligent System for the Delivery of Antisense Oligonucleotides", *J. Liposome Res.*, 7(1)1-18 (1997).

Hafez et al., "Tunable pH-sensitive liposomes composed of mixtures of cationic and anionic lipids", Biophys. J., 79(3): 1438-1446 (2000).

Hafez et al., "Cholesteryl hemisuccinate exhibits pH sensitive polymorphic phase behavior". *Biochim. Biophys. Acta,* 1463(1):107-114 (2000).

Hitoyuki Fukuda et al., "Bilayer-Forming Ion-Pair Amphiphiles form Single-Chain Surfactants", *Journal of the American Chemical Society,* American Chemical Society Washington DC, US.

Kaler et al., "Spontaneous Vesicle Formation in Aqueous Mixtures of Single-Tailed Surfactants", *Science,* 254:1371-1373, Sep. 1989.

Leventis et al., "ph-dependent stability and fusion of liposomes combining ptotonatable double-chain amphiphiles with phosphatidylethanofamine", *Biochem.*, 26(12)3267-3276 (1987).

Ropert et al., "the delivery of Oligonuc*leotides Using pH Sensitive Liposomes",* in *Delivery Strategies Antisense Oligonucleotide Ther.,* S. Akhtar, Ed., pp. 233-245 (1995).

Tachibana et al., Intracellular regulation of macromolecules using pH-sensitive liposomes and nuclear localization signal: qualitative and quantitative evaluation of intracellular trafficking, *Biochem, Biophys. Res. Commun.,* 251:538-544 (1998).

Zi Chen Li et al., "Synthesis of Cholesterol Derivatives with Amino Acid as Hydeophilic Group and the Vesicles Prepared Therefrom", *Chinese Chem. Lett.,* 12(10):1007-1010 (1999).

Hafez et al. (2000), Biophysical Journal, 79:1438-1446.

Kikuchi et al. (1999), Human Gene Therapy, 10:947-955.

Tachibana et al. (1998), Biochemical and Biophysical Research Communications, 251:538-544.

www.Lenntech.com; Distilled, Deionised and Demineralised Water and Measuring of the Purity, 6 pages, 2008.

Transfection into HeLa cells with amphoteric liposomes
(POPC/DOTAP/CHEMS 60/30/10)

Transfection into CHO cells with amphoteric liposomes
(POPC/DOTAP/CHEMS 60/30/10)

AMPHOTERIC LIPOSOMES AND THEIR USE

CROSS REFERENCE TO RELATED APPLICATION

This Application is a continuation-in-part of application Ser. No. 10/081,617, filed on Feb. 21, 2002, now U.S. Pat. No. 7,371,404 the contents of which are incorporated in their entirety by reference.

FIELD OF INVENTION

The invention relates to amphoteric liposomes, which simultaneously comprise positive and negative membrane-based or membrane-forming charge carriers as well as to the use of these liposomes.

BACKGROUND OF INVENTION

The concept of lipids comprises three classes of natural products, which can be isolated from biological membranes: phospholipids, sphingolipids and cholesterol with its derivatives. However, it also comprises synthetically produced materials with similar characteristics. As representatives of these, diacyl glycerols, dialkyl glycerols, 3-amino-1,2-dihydroxypropane esters or ethers and also N,N-dialkylamines are mentioned.

These substances are of technical interest for the preparation of liposomes. One of the uses of these liposomes is as a container for active ingredients in pharmaceutical preparations. For this purpose, an efficient and stable packaging of the cargo, compatibility with body fluids and a controllable and optionally site-specific release of the content are desirable.

It is a disadvantage that it is difficult to combine the two requirements. The tighter and more stable the packaging, the more difficult it is to release the enclosed active ingredient once again. For this reason, liposomes were developed, which change their properties in reaction to external stimuli. Heat-sensitive and pH-sensitive liposomes are known. The pH-sensitive liposomes are of special interest, since this parameter may change under physiological circumstances, such as during the endocytotic absorption of a liposome in cells or during passage through the gastrointestinal tract. According to the state of the art, pH-sensitive liposomes comprise, in particular, cholesterol hemisuccinate (CHEMS).

Cholesterol hemisuccinate is used in admixture with phosphatidyl ethanolamine for the preparation of pH-sensitive liposomes (Tachibana et al. (1998); BBRC 251: 538-544) U.S. Pat. No. 4,891,208). Such liposomes can be endocytized by many cells and in this way are able to transport cargo molecules into the interior of cells, without injuring the integrity of the cellular membrane.

The anionic character of CHEMS is a significant disadvantage. The liposomes, prepared with it, have an overall negative charge and absorbed by cells only with a low efficiency. Therefore, in spite of the transfer mechanism described above, they are hardly suitable for transporting macromolecules into cells.

Cationic liposomes with the highest possible and constant surface charge are used to transport active ingredients into cells (transfection). The overall positive charge of such particles leads to an electrostatic adhesion to cells and, consequently, to an efficient transport into cells. The use of these compounds and of the liposomes, produced therewith is, however, limited to in vitro or ex vitro uses, since such positively charged liposomes form uncontrolled aggregates with serum components.

The limitation to very few pK values, generally to that of the carboxyl group in the cholesterol hemisuccinate (approximately 4.5) is a disadvantage of the pH-sensitive liposomes, which are available according to the state of the art. A further disadvantage of the compounds is the limitation to negative charge carriers. These are not suitable for binding nucleic acids and, frequently also, proteins efficiently.

Cationic liposomes show good bonding of nucleic acids and proteins and are in a position to bring these active ingredients into cells. It is a disadvantage that they cannot be used for in vivo applications.

SUMMARY OF INVENTION

It was therefore an objective to produce the liposomal structures, which
i) permit an efficient inclusion of active in agents;
ii) can transport these active ingredients into biological cells;
iii) are compatible with use under in vivo conditions; and
iv) can be produced simply and inexpensively.

The inventive object is accomplished by amphoteric liposomes, which comprise at least one positive and at least one negative charge carrier, which differs from the positive one, the isoelectric point of the liposomes being between 4 and 8. This objective is accomplished owing to the fact that liposomes are prepared with a pH-dependent, changing charge.

Liposomal structures with the desired properties are formed, for example, when the amount of membrane-forming or membrane-based cationic charge carriers exceeds that of the anionic charge carriers at a low pH and the ratio is reversed at a higher pH. This is always the case when the ionizable components have a pKa value between 4 and 9. As the pH of the medium drops, all cationic charge carriers are charged more and all anionic charge carriers lose their charge.

The following abbreviations are used in connection with the invention:
CHEMS cholesterol hemisuccinate
PC phosphatidyl choline
PE phosphatidyl ethanolamine
PS phosphatidyl serine
PG phosphatidyl glycerol
Hist-Chol histidinyl cholesterol hemisuccinate The membrane-forming or membrane-based charge carriers have the following general structure of an amphiphile:
charge group—membrane anchor The naturally known systems or their technically modified forms come into consideration as membrane anchors. These include, in particular, the diacyl glycerols, diacyl phosphoglycerols (phospholipids) and sterols, but also the dialkyl glycerols, the dialkyl- or diacyl-1-amino-2,3-dihydroxypropanes, long-chain alkyls or acyls with 8 to 25 carbon atoms, sphingolipids, ceramides, etc. These membrane anchors are known in the art. The charge groups, which combine with these anchors, can be divided into the following 6 groups:

Strongly cationic, pKa>9, net positive charge: on the basis of their chemical nature, these are, for example, ammonium, amidinium, guanidium or pyridinium groups or timely, secondary or tertiary amino functions.

Weakly cationic, pKa<9, net positive charge: on the basis of their chemical nature, these are, in particular, nitrogen bases such as piperazines, imidazoles and morpholines, purines or pyrimidines. Such molecular fragments, which occur in biological systems, preferably are, for example, 4-imidazoles (histamine), 2-, 6-, or 9-purines (adenines, guanines, adenosines or guanosines), 1-, 2-or 4-pyrimidines (uraciles, thymines, cytosines, uridines, thymidines, cytidines) or also pyridine-3-carboxylic acids (nicotinic esters or amides).

Nitrogen bases with preferred pKa values are also formed by substituting nitrogen atoms one or more times with low molecular weight alkane hydroxyls, such as hydroxymethyl or hydroxyethyl groups. For example, aminodihydroxypropanes, triethanolamines, tris-(hydroxymethyl)methylamines, bis-(hydroxymethyl)methylamines, tris-(hydroxyethyl)methylamines, bis-(hydroxyethyl)methylamines or the corresponding substituted ethylamines.

Neutral or zwitterionic, at a pH from 4 to 9: on the basis of their chemical nature, these are neutral groups, such as hydroxyls, amides, thiols or zwitterionic groups of a strongly cationic and a strongly anionic group, such as phosphocholine or aminocarboxylic acids, aminosulfonic acids, betaines or other structures.

Weakly anionic, pKa>4, net negative charge: on the basis of their chemical nature, these are, in particular, the carboxylic acids. These include the aliphatic, linear or branched mono-, di- or tricarboxylic acids with up to 12 carbon atoms and 0, 1 or 2 ethylenically unsaturated bonds. Carboxylic acids of suitable behavior are also found as substitutes of aromatic systems. Other anionic groups are hydroxyls or thiols, which can dissociate and occur in ascorbic acid, N-substituted alloxane, N-substituted barbituric acid, veronal, phenol or as a thiol group. Strongly cationic, pKa<4, net negative charge: on the basis of their chemical nature, these are functional groups such as sulfonate or phosphate esters.

Amphoteric charge carriers, pI between 4.5 and 8.5, net positive charge below the pI, net negative charge above the pI: on the basis of their chemical nature, these charge carriers are composed of two or more fragments of the groups named above. For carrying out the invention, it is, initially, immaterial whether the charged groups are on one and the same membrane anchor or if these groups are on different anchors. Amphoteric charge carriers with a pI between 5 and 7 are particularly preferred for implementing the invention.

Strongly cationic compounds are, for example:
DC-Chol 3-β-[N—(N',N'-dimethylethane) carbamoyl] cholesterol,
TC-Chol 3-β-[N—(N',N',N'-trimethylaminoethane) carbamoyl cholesterol
BGSC bisguanidinium-spermidine-cholesterol
BGTC bis-guadinium-tren-cholesterol,
DOTAP (1,2-dioleoyloxypropyl)—N,N,N-trimethylammonium chloride
DOSPER (1,3-dioleoyloxy-2-(6-carboxy-spermyl)-propylamide
DOTMA (1,2-dioleoyloxypropyl)—N,N,N-trimethylarnmonium chloride) (Lipofectin®)
DORIE (1,2-dioleoyloxypropyl)-3-dimethylhydroxyethylammonium bromide
DOSC (1,2-dioleoyl-3-succinyl-sn-glyceryl choline ester)
DOGSDSO (1,2-dioleoyl-sn-glycero-3-succinyl-2-hydroxyethyl disulfide omithine)
DDAB dimethyldioctadecylammonium bromide
DOGS ((C 18)$_2$GlySper3$^+$) N,N-dioctadecylamido-glycolspe rmin (Transfectam®) (C18)$_2$Gly$^+$N,N-dioctadecylamido-glycine
CTAB cetyltrimethylammonium bromide
CpyC cetylpyridinium chloride
DOEPC 1,2-dioleoly-sn-glycero-3-ethylphosphocholine or other O-alkyl-phosphatidylcholine or ethanolamines, amides from lysine, arginine or ornithine and phosphatidyl ethanolamine.

Examples of weakly anionic compounds are: His-Chol histaminyl-cholesterol hemisuccinate, Mo-Chol morpholine-N-ethylamino-cholesterol hemisuccinate or histidinyl-PE.

Examples of neutral compounds are: cholesterol, ceramides, phosphatidyl cholines, phosphatidyl ethanolamines, tetraether lipids or diacyl glycerols.

Examples of weakly anionic compounds are: CHEMS cholesterol hemisuccinate, alkyl carboxylic acids with 8 to 25 carbon atoms or diacyl glycerol hemisuccinate. Additional weakly anionic compounds are the amides of aspartic acid, or glutamic acid and PE as well as PS and its amides with glycine, alanine, glutamine, asparagine, serine, cysteine, threonine, tyrosine, glutamic acid, aspartic acid or other amino acids or aminodicarboxylic acids. According to the same principle, the esters of hydroxycarboxylic acids or hydroxydicarboxylic acids and PS are also weakly anionic compounds.

Strongly anionic compounds are, for example: SDS sodium dodecyl sulfate, cholesterol sulfate, cholesterol phosphate, cholesteryl phosphocholine, phosphatidyl glycerols, phosphatid acids, phosphatidyl inositols, diacyl glycerol phosphates, diacyl glycerol sulfates, cetyl phosphate or lysophospholipids.

Amphoteric compounds are, for example,
Hist-Chol Nα-histidinyl-cholesterol hemisuccinate,
EDTA-Chol cholesterol ester of ethylenediamine tetraacetic acid
Hist-PS Nα-histidinyl-phosphatidylserine or N-alkylcamosine.

BRIEF DESCRIPTION OF THE DRAWINGS

These and other advantages, objects and features of the invention will be apparent through the detailed description of the embodiments and the drawings attached hereto. It is also to be understood that both the foregoing general description and the following detailed description are exemplary and not restrictive of the scope of the invention.

DETAILED DESCRIPTION OF INVENTION

Figure 1A:
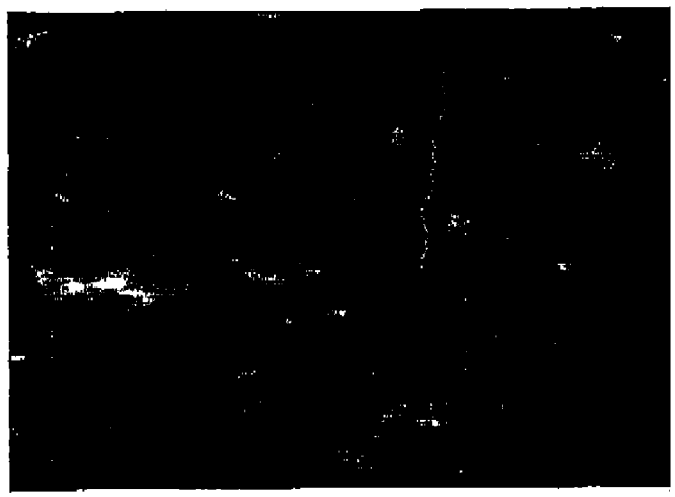
FIGS. 1a/b show microscopic images of Hela or CHO cells transfected with amphoteric liposomes FIG. 2 graphically depicts that in accordance with the invention that the addition of either a phosphatidylcholine or a phosphatidylethanolamine are beneficial for the transfection efficacy of amphoteric liposomes.

According to the invention, liposomes contain variable amounts of such membrane-forming or membrane-based amphiphilic materials, so that they have an amphoteric character. This means that the liposomes can change the sign of the charge completely. The amount of charge carrier of a liposome, present at a given pH of the medium, can be calculated using the following formula:

$$z = \Sigma ni((qi-1)+10^{(pK-pH)}/(1+10^{(pK-pH)})$$

in which $q_i$ is the absolute charge of the individual ionic groups below their pK (for example, carboxyl=0, simple nitrogen base=1, phosphate group of the second dissociation step=−1, etc.)

$n_i$ is the number of these groups in the liposome.

At the isoelectric point, the net charge of the liposome is 0. Structures with a largely selectable isoelectric point can be produced by mixing anionic and cationic portions.

The structures can also be constructed so that, in particular, as the pH drops, the charge on the molecule as a whole is actually changed from negative to positive. Such a reversal of charge is advantageous particularly when the liposomes, produced with these structures, are to be used in physiological interrelationships. Only liposomes with an overall negative charge are compatible with blood and serum components. A positive charge leads to aggregations. Liposomes with a positive charge are, however, very good fusogenically and can transport active ingredients into cells. A pH-dependent reversal of charge therefore permits compounds to be constructed, which are compatible with serum because they have a negative charge; however, after their endocytotic absorption, their charge is reversed and they become fusogenic only in the cell.

In a preferred embodiment of an embodiment of the invention, the amphoteric liposomes have an isoelectric point between 5 and 7.

The invention also relates to amphoteric liposomes, which comprise at least one amphoteric charge carrier, the amphoteric charge carrier having an isoelectric point of between 4 and 8.

In a preferred variation, the amphoteric charge carrier of the liposomes has an isoelectric point of between 5 and 7.

The invention also relates to amphoteric liposomes, the liposomes comprising at least one amphoteric charge carrier and an anionic and/or cationic charge carrier.

It is appropriate that, in a preferred variation, the amphoteric liposomes have an isoelectric point between 5 and 7.

In a special variation of the invention, the inventive liposomes comprise phosphatidyl choline, phosphatidyl ethanolamine, diacyl glycerol, cholesterol, tetraether lipid, ceramide, sphigolipid, and/or diacyl glycerol. However, the preparation of the liposomes can, of course, be carried out with many lipid combinations of the inventive teachings. For examples, liposomes can be synthesized using a large amount of CHEMS (about 40%) and a smaller amount of DOTAP (about 30%). At the pK of the carboxyl group of the CHEMS, the negative charge of this component is already suppressed so far, that the positive charge carrier predominates overall.

An alternative formulation is the mixing of C HEMS with HisChol the stronger charging of the positive charge carrier HisChol going along synergistically with the discharging of the negative CHEMS.

If Hist-Chol, which in itself is amphoteric, is incorporated in a neutral membrane of, for example, phosphatidyl choline, an arnphoteric liposome with an isoelectric point, which largely corresponds to that of Hist-Chol, also results.

It is known to those skilled in the art how the important parameters can be adapted by manifold variations of the inventive teachings:

(i) the charge density of the liposomes at the end points of the charge reversals by the amount and the pKa values of the charge carriers used, (ii) the slope of the charge reversal curve by the ratio of the two charge carriers, by their absolute amounts and by an optimally synergistic effect of two complementary pH-sensitive lipids and (iii) the passing of the zeta potential through zero due to the ratio of the two charge carriers or also due to the position of the pK value or values.

In a further variation of the invention, the liposomes have an average size of between 50 and 1000 nm, preferably of between 70 and 250 nm and particularly between 60 and 130 nm. The amphoteric liposomes are synthesized by methods known in the art, such as the injection of ethanol into a lipid solution in an aqueous buffer, by hydrating dry lipid films or by detergent dialysis. The size of the liposomes can vary, generally between 50 nm and 10,000 nm. Homogeneous populations can be produced by high-pressure homogenization or by extrusion.

In a preferred variation of the invention, the liposomes comprise an active ingredient.

Advisably, in a preferred variation, the active ingredient is a protein, a peptide, a DNA, an RNA, an antisense nucleotide and/or a decoy nucleotide.

In a further preferred variation of the invention, at least 80% of the active ingredient in the interior of the liposome.

The invention also relates to a method for charging a liposome with active ingredient, a defined pH being used for the encapsulation and the pH being adjusted to a second value for separating the unbound material.

The invention furthermore also relates to a method for charging a liposome with active ingredient, the liposomes being permeabilized and closed at a defined pH.

The invention also relates to the use of the liposomes for the preparation of nanocapsules by depositing polymers or polyelectrolytes on the lipid layer. Such substances can be precipitated once or several times on the surface. With a repeated deposition, which optionally can be carried out in the absence of cross-linking agents, liposomal nanocapsules of the type described in the WO 00/28972 or in the WO 01/64330 are formed. It is advantageous that the electrostatic interaction with the polyelectrolyte can be interrupted when the substances described here are used. It is known that the interaction of a polyelectrolyte with charge carriers of the liposomal membrane can lead to the de-mixing of membrane components and to the formation of lipid clusters. In many cases, this de-mixing is associated with a permeabilization of the liposome. The inventive substances enable this interaction to be switched off after the coating process. The liposomes are enclosed only sterically in the nanocapsules if the pH is increased at this time and there no longer is any interaction between the membrane and the polyelectrolyte. Cluster formation of the lipids and the permeabilization of the membrane, associated therewith, can thus be avoided.

The invention also relates to the use of the inventive liposomes for packaging and releasing active ingredients. In this variation, the liposomes bring about, in particular, the efficient packaging of active ingredients, such as nucleic acids. Nucleic acids are incubated with said lipids particularly at a low pH (about 3 to 6). After the formation of the liposomes, nucleic acids, adhering to the outside, can be washed off by changing to a high pH (about 7 to 9).

An analogous procedure can be used to package proteins. Advantageously, the pH of the medium is adjusted to a value here, which lies between the pH of the liposome and that of the protein. It has proven to be particularly advantageous, if the two pI values are more than one unit apart.

In a further variation of the invention, the liposomes are used to prepare release systems in diagnostics.

In a further preferred variation of the invention, the liposomes are used as transfection systems, that is, for bringing active ingredients into cells.

In a further variation of the invention, the liposomes are used for the controlled release of their contents by fusion or permeabilization of the membrane. For example, liposomes of a lipid, which by itself is not membrane-forming, can be stabilized by the incorporation of charge carriers, such as PE. If the charge carrier is transformed into a neutral, uncharged or zwitterionic state, the permeability of the membrane is increased. Known liposomes of the state of the art (PE/CHEMS, Tachibana et al.) permit such a permeabilization at the low pH values, which are attained under physiological conditions only in the interior of endosomes or during passage through the stomach. Amphoteric liposomes can be produced by the measures listed above in such a manner, that their neutral point lies at any desirable pH between 4 and 9. Under these conditions, the liposomes are permeable and can deliver cargo to the medium.

However, the liposomal formulations can be produced, processed and stored under conditions of lesser permeability. In a preferred embodiment of the invention, liposomes are produced so that they release of their cargo under conditions of a physiological pH, but enclose their cargo securely at a low pH. Such liposomes are suitable particularly for the preparation of formulations with slow release kinetics, the release being initiated only by contact with body fluids and not during storage or transport.

A preferred embodiment of the inventive teaching therefore consists of the use of such liposomes for therapeutic purposes, especially for such uses, which employ the specific targeting of the liposomes. The slight nonspecific binding is a prerequisite here for transporting the liposomes to the target place. In contrast to this, a high nonspecific binding would prevent any transport of the liposomes to the target place. A specific binding can be attained by further measures of the state of the art, that is, by selecting the size of the liposomes or also by binding the ligands to the liposomal surface, which binds to a target receptor of the cell surface. Ligands may, for example, be antibodies or their fragments, sugars, hormones, vitamins, peptides, such as arg-gly-asp (RGD), growth factors, bilirubin or other components.

The preferred variation of the inventive teachings relates to the use of the liposomes for therapeutic or diagnostic applications under in vivo conditions. Preferably, such liposomes are ones, which have a slight nonspecific binding and, with that, a slight tendency to fuse under physiological conditions, but are combined strongly and with a high fusion competence under changed conditions. Such liposomes are amphoteric liposomes, which have an overall anionic particle charge under physiological conditions and an increasingly cationic charge at a pH below 6.5. Such pH values occur during the endocytosis of the liposomes into cells. Such pH values also occur in the interior of tumors and in the external layers of the skin. Low pH values can also be obtained by perfusing an organ ex vivo for a certain period of time. A high binding strength and fusion competence is therefore limited to those liposomes, which were already taken up by cells or special tissue. The binding strength and increasing fusion competence support the fusion of the liposomal membrane with the cell membrane. This event leads to a direct release of the cargo into the interior of the cell without releasing components of the lysis of the endosome and, with that, endangering the cargo or cell components.

Furthermore, the use of the liposomes as a sustained release formulation and/or as a circulating depot is appropriate. The liposomes can also be used advantageously for intravenous or peritoneal application. In a particularly preferred variation of the invention, the liposomes are used as a vector for the in vivo, in vitro and ex vivo transfection of cells.

The inventive liposomes have several advantages. Cationically chargeable liposomes of 40 percent HisChol and PC bind the nucleic acids, such as DNA, to their membrane even under conditions of a neutral pH. Surprisingly, this binding is suppressed completely if the above-mentioned liposomes are produced using 5 percent of PG in addition and then have amphoteric properties. However, the binding of nucleic acids to the membrane can be restored once again by decreasing the pH. The inventive liposomes are therefore particularly well suited for the pH-dependent binding of nucleic acids.

Furthermore, it was surprisingly found that a series of proteins also behaves in the manner described for nucleic acids. For example, antibodies bind not at a neutral pH, but under slightly acidic conditions effectively to the membrane of the inventive liposomes. Such a behavior cannot be observed in the case of pH-sensitive liposomes from a neutral lipid and CHEMS nor from such a liposomes from a neutral lipid and HisChol. It is therefore a special property of the amphoteric liposomes. Surprisingly, it was also found that inventive liposomes, contrary to the known, constitutive, cationic liposomes, are compatible with serum. An appropriate embodiment of the inventive teachings therefore consists of the use of such liposomes for therapeutic properties. It is an advantage of the liposomes that, in comparison to known, constitutive, cationic liposomes, the nonspecific binding to cells is significantly less.

It is, however, also surprising that the fusion competence of the inventive liposomes depends on the pH of the medium. In comparison to biological membranes of cells, the fusion competence is determined by the lipid selected and also by the charging of the liposomes. Usually, a binding step precedes the actual fusion. However, strong binding of the liposomes to cell membranes is not always desirable and should take place, as described above, only under controlled conditions in particular cells or tissue.

The liposomes can therefore be used to construct liposomal vectors for the transport of active ingredients into cells. All materials, which do not form micelles, come into consideration as active ingredients. Water-soluble materials are particularly suitable as active ingredients. They include many proteins and peptides, especially antibodies or enzymes or antigens, all nucleic acids, independently of their molecular weight and their derivation from RNA or DNA. However, they include also other biological macromolecules, such as complex sugars, natural products and other compounds, as well as low molecular weight active ingredients of synthetic or natural origin, which otherwise cannot penetrate through the cell membrane as barrier. With the help of vectors, such materials can then be transported into the interior of cells and initiate actions, which are not possible without this transport.

Accordingly, with the help of the inventive teachings, liposomes can be prepared, the fusion and binding properties of which differ at different pH values. Serun-compatible liposomes, which are laden with a large amount of active ingredients and transport these into the interior of cells, can therefore be produced in this way. Someone, skilled in the art, is able to combine elements of the inventive teachings with one another and, with that, produce liposomes, which are optimally suitable for a particular purpose.

The invention is described in greater detail in the following by means of examples without being limited to these examples.

EXAMPLE 1

Preparation and Charge Properties of Amphoteric Liposomes with Charge Carriers, which can be Charged Positively and are Constantly Charged Negatively His-Chol (5 mg) and 7.8 mg of POPC and 2 mg of DPPG are dissolved in 4 ml of a 1:1 (v/v) mixture of chloroform and methanol and dried completely in a rotary evaporator. The lipid film is hydrated with 4.3 mL of the appropriate buffer (10 mM KAc, 10 mM HEPES, 150 mM NaCl, pH 7.5, in a lipid concentration of 5 mM by a five-minute treatment with ultrasound. Subsequently, the suspension is frozen and, after thawing, extruded several times (Avestin LiposoFast, polycarbonate filter with a 200 nm pore width). For measuring the zeta potential, the final concentration of the liposomes is adjusted to a value of 0.2 mM. For the dilution, the buffer system, named above, is used at a pH of 7.5 or 4.2. The zeta potentials measured lie between −18 mV (at pH 7.5) and +35 mV (at pH 4.2).

EXAMPLE 2

Preparation and Charge Properties of Amphoteric Liposomes with Constant Positive and Variable Negative Charge Carriers POPC, DOTAP and CHEMS are dissolved in the molar ratios given below in 4 mL of a 1:1 (v/v) mixture of chloroform and methanol and evaporated completely in the rotary evaporator. The lipid film is hydrated with 4.3 mL of the appropriate buffer (10 mM KAc, 10 mM HEPES, 150 mM NaCl, pH 7.5, in a total lipid concentration of 5 mM by a five-minute treatment with ultrasound. Subsequently, the suspension is frozen and, after thawing, extruded repeatedly (Avestin LiposoFast, polycarbonate filter with a 200 nm pore width). The Table below shows the zeta potentials as a function of pH.

Composition of the liposomes in mole percent

| liposome 1 | POPC 50 | DOTAP 40 | Chems 10 |
| liposome 2 | POPC 50 | DOTAP 30 | Chems 20 |
| liposome 3 | POPC 50 | DOTAP 25 | Chems 25 |
| liposome 4 | POPC 50 | DOTAP 20 | Chems 30 |
| liposome 5 | POPC 50 | DOTAP 40 | Chems 10 |

TABLE 1

Zeta Potentials in mV

| pH | Liposome 1 | Liposome 2 | Liposome 3 | Liposome 4 | Liposome 5 |
|---|---|---|---|---|---|
| 4 | 44.2 | 38.4 | 34.7 | 31.7 | 16.2 |
| 5 | 39.9 | 25.6 | 27.2 | 22.1 | 3.3 |
| 6 | 37 | 21.4 | 16.4 | 2.5 | −7.3 |
| 7.5 | 29.2 | 1.8 | −7.9 | −18.9 | −34.6 |

The height of the zeta potential and its slope can be selected within why limits by means of a suitable composition.

EXAMPLE 3

Preparation and Charge Properties of Amphoteric Liposomes with Complete Switchability in One Compound Hist-Chol (5 mg) and 9.8 mg of POPC are dissolved in 4 ml of a 1:1 (v/v) mixture of chloroform and methanol and dried completely in a rotary evaporator. The lipid film is hydrated with 4.3 mL of the appropriate buffer (10 mM KAc, 10 mM HEPES, 150 mM NaCl, pH 7.5, in a lipid concentration of 5 mM by a five-minute treatment with ultrasound. Subsequently, the suspension is frozen and, after thawing, extruded several times (Avestin LiposoFast, polycarbonate filter with a 200 nm pore width) , The course of the zeta potential at different pH values and ionic strengths is shown in the table below (Table 2).

TABLE 2

| pH | Without Salt | 100 mM of NaCl |
|---|---|---|
| 4 | 45.6 | 20.2 |
| 5 | 26.9 | 2.2 |
| 6 | −4.1 | −5.2 |
| 7 | −31.4 | −15.3 |
| 8 | −45.7 | −25.4 |

EXAMPLE 4

Serum Aggregation

Lipid films are prepared as in Example 1. A lipid mixture, which did not contain any DPPG, was used as comparison sample. The lipid films were hydrated in buffer (10 mM of phosphate, 150 mM of sodium chloride, pH of 7.4) and extruded as above. Human serum is diluted with an equal amount of buffer (10 mM of phosphate, 150 mM of sodium chloride, pH of 7.4), particular components and fat being removed by centrifuging (20 minutes, 13,000 rpm, 4° C.); the clear serum is filtered sterile with a filter having a pore width of 0.2 µm.

The liposomes, prepared above are added to the serum in concentration of 1 mM and incubated for 15 minutes at 37° C. After the incubation, the suspension of the DPPG-containing liposomes is uniformly cloudy; however, flocculation cannot be observed. The diameter of the liposomes is determined by means of dynamic light scattering and is changed by less than 10% from that of the starting sample. The suspension of the DPPG-free liposomes clearly shows flocculation.

EXAMPLE 5

Serum Stability of the Membrane

Aside from serum aggregation, the precipitation of an active ingredient (carboxyfluorescein, CF) in the presence of human serum was also investigated. For this purpose, POPC/DOTAP/CHEMS liposomes of different composition were prepared by the method of Example 2: POPC 100% (as control), POPC/DOTAP/CHEMS 60:30:10, 60:20:20 and 60:10:30 (in mole %). Any CF, which is not enclosed, was removed by gel filtration. For the measurement, the liposomes were diluted to 0.1 mM in serum and incubated at 37° C. A 30 µL sample was removed at certain times and diluted to 300 µL with 100 mM of tris buffer, having a pH of 8. 2 and the fluorescence was measured. The 100% values were obtained by dissolving the liposomes with 10 µL of Tritron X-100 (10% in water). The enclosed CF as a function of time is shown in the Table below.

The liposomes lose only a little CF into the serum during the 4-hour period of measurement. POPC/DOTAP/CHEMS 60:30:10 and 60:20:20 still contain about 75%, POPC and POPC/DOTAP/CHEMS 60:10:30 even 100% of their original CF content (see Table 3).

TABLE 3

| Time in Min. | POPC | POPC/DOTAP/ CHEMS 60:30:10 | POPC/DOTAP/ CHEMS 60:20:20 | POPC/DOTAP/ CHEMS 60:10:30 |
|---|---|---|---|---|
| 0 | 100% | 100% | 100% | 100% |
| 15 | 91% | 84% | 95% | 107% |
| 60 | 94% | 81% | 87% | 110% |
| 120 | 96% | 80% | 76% | 105% |
| 240 | 96% | 80% | 77% | 107% |

EXAMPLE 6

Binding DNA

Liposomes of the following compositions (in mole %) are prepared as in Example 1 (all data is in mole %).

| A: | 60 POPC | 40 HisChol | | |
|---|---|---|---|---|
| B: | 55 POPC | 40 HisChol | 5 | CHEMS |
| C: | 60 POPC | 20 HisChol | 20 | CHEMS |

The liposomes are suspended in a concentration of 0.2 mM in buffer (10 mM of potassium acetate, 10 mM of HEPES, pH 4.2 or 7.5). A DNA solution (45 μL, 1 mg of DNA (Hering sperm, SIGMA D3159) in 1 mL of water) are added in each case to 1 mL of the different liposomes samples and mixed quickly. After an incubation period of 15 minutes, the sample is filled up with 6 mL of the appropriate buffer and the zeta potential of the liposomes is measured (Table 4).

TABLE 4

| | pH 4.2 | | pH 7.5 | |
|---|---|---|---|---|
| Lipid | −DNA | +DNA | −DNA | +DNA |
| A | +47.6 | −32.0 | +2.4 | −44.4 |
| B | +47.8 | −28.1 | +0.1 | −38.4 |
| C | +34.0 | −28.6 | −10.1 | −24.7 |

Under the conditions of an excess of cationic charges (pH 4:2), there is a strong reversal of the charge of the particles. At a neutral pH of 7.5, the CHEMS in high concentration (liposome C) can overcompensate the charge of the HisChol and the particles have a negative zeta potential. Only slight amounts of DNA bind to such particles.

EXAMPLE 7

Binding and Detaching DNA

Liposomes having the compositions POPC/DOTAP/CHEMS in the ratio of 60:15:25 and POPC/DCChol/CHEMS in the ratio of 60:15:25 (in mole %), were prepared by the method of Example 2. The binding of the DNA was carried out at a pH of 4.2 by the method of the above example and the zeta potentials were determined. Subsequently, the pH of the samples was adjusted to a value of 7.5 and the zeta potential was measured once again.

| | Mixture | Zeta (mV) |
|---|---|---|
| a) | POPC/DCChol/CHEMS 60:15:25 (pH 4.2) (aggregate) | −43.5 |
| b) | POPC/DOTAP/CHEMS | −43.7 |
| c) | POPC/DCChol/CHEMS | −18.5 |

-continued

| | Mixture | Zeta (mV) |
|---|---|---|
| d) | POPC/DOTAP/CHEMS | −14.5 |

In the presence of DNA, a negative zeta potential is measured at a low pH; however, the original particles were charged positively. After the change to the neutral pH, this charge, which is due to the DNA, is decreased. The zeta potentials approach that of the untreated liposomes (−11 mV at a pH of 7.5).

EXAMPLE 8

DNA Inclusion and Detachment of Material not Encapsulated

Two liposome formulations, having compositions of POPC60/DOTAP15/CHBEMS25 and POPC85/DOTAP15 respectively, are prepared as dry lipid films as described above. In each case, the total amount of lipid was 4 μmoles. For hydration, Herings DNA was dissolved in 10 mM of potassium acetate, 10 mM of HEPES and 100 mM of sodium chloride at a pH of 4.0. The DNA (4 mg) was added directly to the lipid films. The resulting liposomes were frozen and thawed repeatedly and subsequently extruded through a 200 nm filter.

Each 500 μL of particles was mixed with 2.5 mL of a sucrose solution (0.8 M sucrose in the above buffer, at a pH of 4.0 or 7.5). Over this, 1.5 mL of a 0.5 M sucrose solution and 0.5 mL of the buffer were placed.

Liposomes were then separated by flotation from unbound DNA. After the flotation, the liposomes were removed from the buffer/0.5 M sucrose interface. The amount of bound DNA was determined by intercalation of propidium iodide. The Stewart assay was used to determine the amount of lipid. Only the PC used responds in the Stewart assay. The other lipids were not calculated by means of this value. The results are shown in the Table below (Table 5).

TABLE 5

| | Liposome | |
|---|---|---|
| | pH 4.0 | pH 7.5 |
| POPC/DOTAP/CHEMS 60/15/25 | 2 μg DNA/μg DOTAP | 1.2 μg DNA/μg DOTAP |
| POPC/DOTAP 85/15 | 2.3 μg DNA/μg DOTAP | 2.3 μg DNA/μg DOTAP |

With the amphoteric liposomes, only about half of the bound DNA floats up after the change in pH to 7.5. This material is the actually enclosed material. Similar results are obtained by digesting with DNAse DNA cannot be detached once again from constitutively cationic liposomes by changing the pH or by additionally increasing the ionic strength and always remains on the outside.

EXAMPLE 9

Fusion Properties

Liposomes with the following compositions are prepared as in Example 1 (all data in mole %):

| | | | | | |
|---|---|---|---|---|---|
| A) | POPC 60 | HisChol | 40 | | |
| B) | POPC 55 | HisChol | 40 | CHEMS | 5 |
| X) | POPC 100 | | | | |
| Y) | POPC 60 | DPPG 40 | | | |

The facultative cationic liposomes A or B are incubated with the neutral liposomes X or the anionic liposomes Y in the buffer (10 mM HEPES, 10 mM potassium acetate, pH 4.2 or 7.5). The possible fusion of liposomes is analyzed by size measurement by means of dynamic light scattering (Table 6).

TABLE 6

| Liposome 1 | X | X | Y | Y |
|---|---|---|---|---|
| Liposome 2 | A | B | A | B |
| pH 4.2 | 161.6 nm | 191.9 nm | 1689.3 nm | 2373.2 nm |
| pH 7.5 | 191.8 nm | 202.4 nm | 250.0 nm | 206.3 nm |

The starting sizes of the liposomes were 161.8 nm at pH 4.2 and 165.9 nm at pH 7.5
A) 183.2 nm
X) 195.2 nm
Y) 183.2 nm The size of the pairs with the complementary charge (YA and YB) differs clearly from the size of the mixed suspensions with the neutral liposome X. The extent of the interaction is determined by the magnitude of the charge of the facultative cationic liposomes. The extent of the fusion to larger units does not depend on the fusogenic lipid PE.

EXAMPLE 10

Permeability to Macromolecules

DOPE (13.75 μmoles), 2.5 μmoles of CHEMS and 10 μmoles of HisChol are dissolved in isopropanol and the solvent is drawn off under a vacuum. A solution (2.5 mL) of proteinase K in buffer (1 mg/mL of proteinase K, 10 mM of potassium acetate, 10 mM HEPES, 150 mM of sodium chloride, pH 4.2) is added to the dried lipid film. After the film is hydrated, the liposomes formed are extruded through a 400 nm membrane. Proteinase, which is not enclosed, is removed by floatation of the liposome in the sucrose gradient. The liposomes, so produced, are incubated with 7.5 ml of buffer at a pH of 4.2 and 7.2 (buffer as above, starting pH 4.2 and 8.0). After the combination, the proteinase K released is removed using a 0.1 μm membrane. The liposomes, remaining in the filter, are then treated with 7.5 mL of a solution of Triton X-100 in buffer (as above, pH 8.0).

All filtrates are tested for the presence of proteinase K. For this purpose, a solution of azocasein (6 mg/mL of azocasein in 1 M urea, 200 mM tris sulfate, pH 8.5) is used. This solution (500 μL) is mixed with 100 μL of filtrate or buffer and incubated for 30 minutes at 37° C. The reaction is terminated by the addition of 10% trichloroacetic acid. Precipitated proteins are removed by centrifuging. The coloration is measured at 390 nm (Table 7).

TABLE 7

| pH of Incubation | Triton X-100 | Absorption at 390 nm Blank |
|---|---|---|
| 4.2 | − | 0.0192 |
| 4.2 | + | 0.2345 |

TABLE 7-continued

| pH of Incubation | Triton X-100 | Absorption at 390 nm Blank |
|---|---|---|
| 7.2 | − | 0.2210 |
| 7.2 | + | 0.0307 |

If the incubation of the liposomes is carried out at a pH of about 4.2, very little if any proteinase K is released. Only the dissolution of the liposomes with Triton X-100 leads to the release of the enzyme. If the liposomes are incubated at a pH of 7.2, the bulk of the enzyme is released already without the addition of the Triton and is found in the first filtrate. Hardly any additional enzyme is then dissolved from the liposomes by the addition of Triton.

EXAMPLE 11

Protein Binding

Liposomes, having the composition POPC50/DOTAP10/CHEMS40 (all data in mole %) are prepared as in the preceding examples. A solution of 0.26 mg/mL of lysozyme in buffer (10 mM MES of pH 5.0 or pH 6.0 or 10 mM of HEPES of pH 7.0 or pH 8.0) is used to hydrate the lipid film. After the hydration, all samples were frozen and thawed repeatedly. Subsequently the liposomes are homogenized by ultrasound and extruded through a 200 nm filter.

The liposome suspension, so prepared, is adjusted to a pH of 4.0 by the addition of acetic acid, Subsequently the liposomes are separated by flotation from protein, which has not been incorporated. The proportion of enclosed protein is given in the Table below (Table 8).

TABLE 8

| pH during Inclusion | % of Material Enclosed |
|---|---|
| 5.0 | 4 |
| 6.0 | 21 |
| 7.0 | 75 |
| 8.0 | 80 |

Liposomes of the composition used show a pI of 5; the lysozyme is a basic protein with a pI of 11.5. The two partners therefore have opposite charges at a pH between 6 and 8. An efficient inclusion in the liposomes is brought about by electrostatic attraction. Protein, not encapsulated, was removed at a pH of 4. The interaction between the partners is canceled at this pH.

EXAMPLE 12

Transfection into Cells

Figure 1B:

HeLa cells or CHO cells ($3 \times 10^5$) were plated into each cavity of a 6-well titer plate and cultured for three days. Liposomes (POPC/DOTAP/CHEMS 60/30/10) were prepared in the presence of fluorescence-labeled dextran (TRITC dextran 10 mg/mL in the hydration buffer). TRITC dextran, which had not been incorporated, was removed by gel filtration. The liposomes, so prepared, were added to the cells and incubated for 6 hours at 37° C. Subsequently, the cells were washed twice with buffer. The absorption of dextran was followed in the microscopic image. The results are shown in FIG. 1.

EXAMPLE 13

Ligand Binding and Transfection

Liposomes, having the composition of POPC/DOTAP/Chems/N-glutaryl-DPPE (50:10:30:10 (mole %)) are prepared as in Example 2. At the same time, they are hydrated with a solution of 3 mg/mL of TRITC-Dextran (having a molecular weight of about 4,400) in HEPES 10 mM and 150 mM of sodium chloride at a pH of 7.5. TRITC-Dextran, which is not enclosed, is removed by gel filtration through a Sephadex G-75 column. Activation of the N-glutaryl DPPEs with EDC (1-ethyl-3-(3-dimethylaminopropyl carbodiimide) (3.5 mg of EDC per 400 μL of liposome suspension) and subsequent stirring in the dark for 5 hours brings about the binding of the cyclic peptide RCDCRGDCFC to the liposomal surface. The RGD peptide (250 μg in 150 RL of buffer) was then added and stirring was continued overnight. The liposomes were separated by gel filtration from the peptide, which had not been bound.

Human endothelium cells (HUVEC) were cultured in a special medium. The liposomes, modified with ligand, and control liposomes without RGD ligand were added as a 0.5 mM suspension to the cells. After 2 hours, the liposomes are removed and the cell chambers rinsed 3 times with PBS buffer and viewed under the fluorescence microscope. The TRITC fluorescence of cells, which had been treated with RDG liposomes, is distinctly redder than that of the control liposomes.

EXAMPLE 14

Pharmacokinetics (Blood Level and Organ Distribution of pH-Switchable Liposomes)

Liposomes of POPC/Chol (60:40), POPC/Hist-Chol/Chol (60:20:20) and POPC/IDOTAP/Chems (60:10:30) (500 μL) were injected into the tail vein of male Wistar rats.

Liposome suspensions (50 mM) were prepared by hydrating a lipid film of the corresponding formulation (addition of 0.03 moles of $^{14}$C-DPPC) with 2 mL of a solution of 1 mg $^3$H-inulin in HEPES 10 mM, sodium chloride 150 nm at a pH of 7.5). After 3 freezing and thawing cycles, the suspensions were extruded repeatedly through a 400 nm membrane (LiposoFast, Avestin). [3]H-Inulin which had not been enclosed, was removed by gel filtration though a G-75 Sephadex-column and subsequent concentration over CENTRIPREP (Millipore) centrifuging units.

Liposome suspension (0.5 mL) was administered to 4 experimental animals per formulation and blood samples were taken after 5 minutes, 15 minutes, 60 minutes, 3 hours, 12 hours and 24 hours. The radioactivity of the membrane fraction and of the soluble cargo was measured by scintillation and gave the following values: Elimination half-life times from the blood

| | |
|---|---|
| POPC/Chol | greater than 120 minutes |
| POPC/DOTAP/Chems | greater than 120 minutes |
| POPC/Hist-Chol | greater than 120 minutes |

With their relatively long half-life in the blood, the inventive liposomes fulfill the basic prerequisites for a vector system. They are not acutely toxic and not absorbed immediately by their reticuloendothelial system. Up to the end of the experiment, the ratio of the 3[H] to the 14[C] radioactivity of the blood samples was constant. Release of the cargo by complement lysis therefore does not take place in any of the cases.

EXAMPLE 15

Transfection Efficiency of Amphoteric Liposomes Comprising Neutral Lipids as well as Anionic and Cationic Lipids.

Transfection efficiency (a functional measure) of amphoteric liposomes is significantly enhanced upon the addition of neutral lipids. The transfection efficiency of various amphoteric liposomal formulations loaded with an antisense oligonucleotide targeting Eg5, a protein critical for mitosis, was measured. Eg5 inhibition results in the arrest of cell division and induces apoptosis.

Fifty microliters (50 μl) of the various lipid mixtures in ethanol were placed into individual wells of a 96 well multititer plate. Next, 115 μl of a buffer (HAc 10 mM, NaCl 50 mM, pH 4.5) containing an Eg5 antisense oligonucleotide was added and rapidly mixed with the lipids resulting in a final ratio between the cationic lipid and backbone phosphate charges of the oligonucleotide of between 2 and about 5. The resulting solution was about 30% ethanolic and in a subsequent step the pH was adjusted using 750 μl $Na_2HPO_4$ 27 mM, NaCl 140 mM, pH 8.0. The final dispersion was about 5.5% ethanol at a pH of 7.5.

HeLa cells were grown to about 25% confluence in DMEM with 10% fetal calf serum (FCS) at 37° C. and 5% $CO_2$. For transfection, the medium was changed to Optimem and the various liposomal formulations were added to a final oligonucleotide concentration of 15 nM. Positive controls were performed using Oligofectamin according to manufacturer instructions to transfect the Eg5 antisense oligonucleotide at a concentration of 30 nM oligonucleotide. An unrelated oligonucleotide that does not interfere with cell division was also used and had no effect on cell survival. After about a 4 hour incubation, the medium was completed by adding FCS in DMEM and cells were grown for about 3 days. Living cells were quantified using Cell Titer Blue. The survival of untransfected cells was set at 100% and the survival of cells transfected with Eg5 using Oligofectamin was set at 0%. Growth inhibition for cells transfected with the various liposomal formulations is expressed as %inhibition (Eg5)/%inhibition (control oligo).

Amphoteric liposomes were formulated using a strong cation ( DOTAP), a weak anion (oleic acid (OA) or dioleoylglycerol hemisuccinate (DOGS)), and increasing amounts of a neutral lipid (POPC or DOPE). The ratio of the anion:cation was maintained at about 1.5-2.0 to 1 in all formulations. For all three formulations, transfection was significantly enhanced with the addition of about 10-20% neutral lipid. This experiment demonstrates that the chemical nature of the membrane anchor for the lipids does not influence the fusogenicity of the liposomes in the presence of neutral lipids. OA is a monocarboxylic acid grafted onto a monoalkyl chain, whereas DOGS has the same charged moiety, but is combined with a diacylglycerol anchor.

Figure 2:
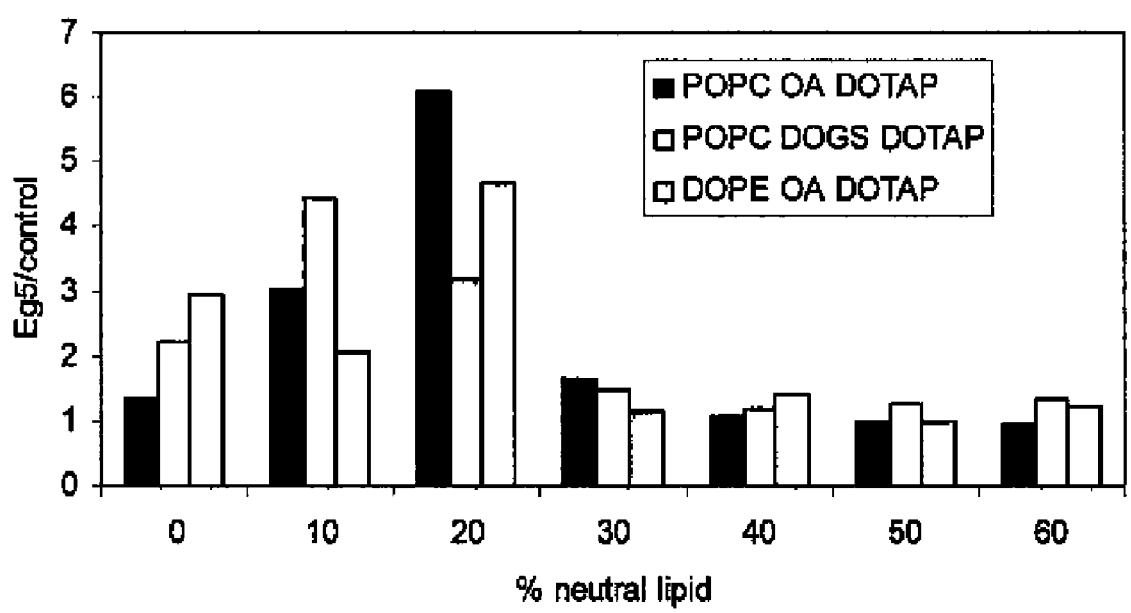

The experiment results, are depicted in FIG. 2, shows that addition of either a phosphatidylcholine or a phosphatidylethanolamine are beneficial for the transfection efficacy of the amphoteric liposomes.

EXAMPLE 16

Figure 3:
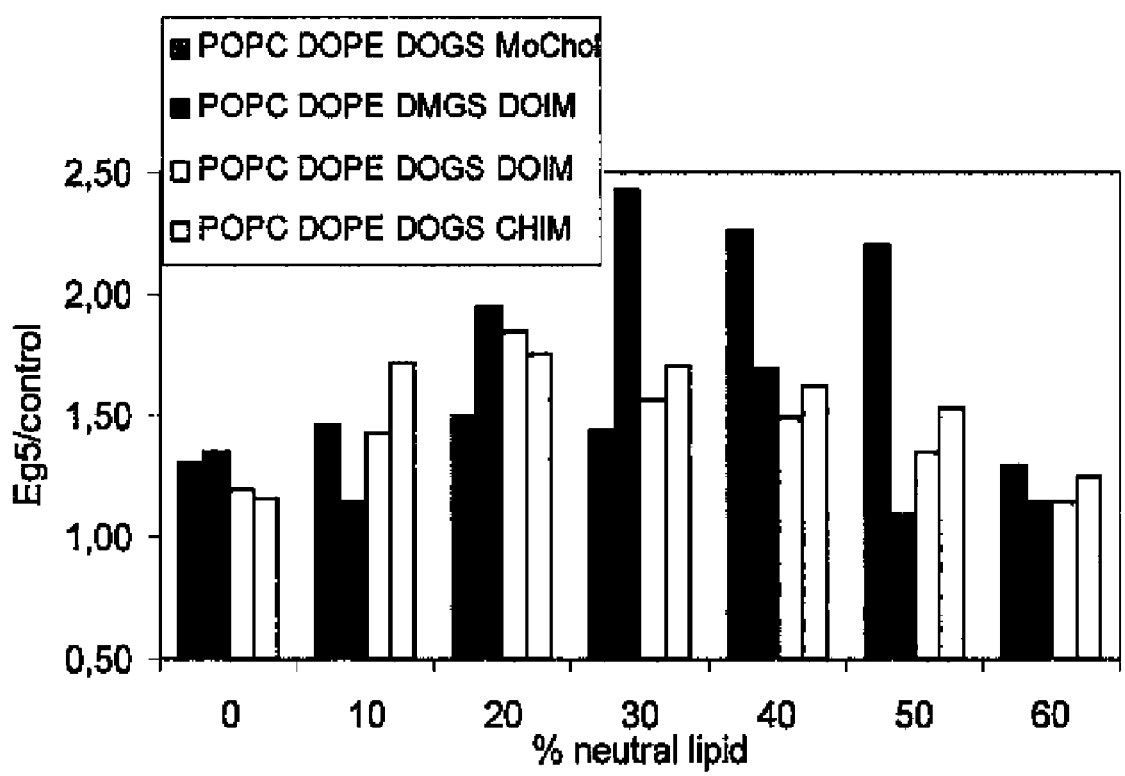
FIG. 3 graphically depicts that in accordance with the invention that the chemical nature of the membrane anchor for the lipids does not influence the fusogenicity of the liposomes in the presence of neutral lipids.

Chemical Nature of the Membrane Anchor for the Lipids does not Influence the Fusogenicity of the Liposomes in the Presence of Neutral Lipids Amphoteric liposomes were formulated using a weak cation (4-(2-aminoethyl)-morpholino-cholesterolhemisuccinate (MoChol), 4-(2,3-bis-oleoyloxy-propyl-1-methyl-1H-imidazole (DOIM) or histaminyl-cholesterolcarbamate (CHIM), a weak anion (dioleoylglycerol hemisuccinate (DOGS) or dimyristoylglycerol hemisuccinate (DMGS)), and a combination of neutral lipids (POPC and DOPE). The ratio of the anion:cation was maintained at about 2:3 in all formulations. Transfection was significantly enhanced with the addition of about 20-50% $ neutral lipids, depending upon the anion/cation combination. Higher concentrations of neutral lipid did not enhance liposomal transfection. This experiment demonstrates, as depicted in FIG. 3, that the chemical nature of the membrane anchor for the lipids' does not influence the fusogenicity of the liposomes in the presence of neutral lipids. MoChol and CHIM are based on cholesterol whereas the other lipids are based on diacylglycerol. Also, saturated lipid components (DMGS) or unsaturated (DOIM and DOGS) components react similarly to the inclusion of neutral lipids.

EXAMPLE 17

Mixtures Comprising Genuine Amphoteric Lipids Benefit from the Addition of Neutral Lipid in Terms of Functional Cell Transfection.

Figure 4:
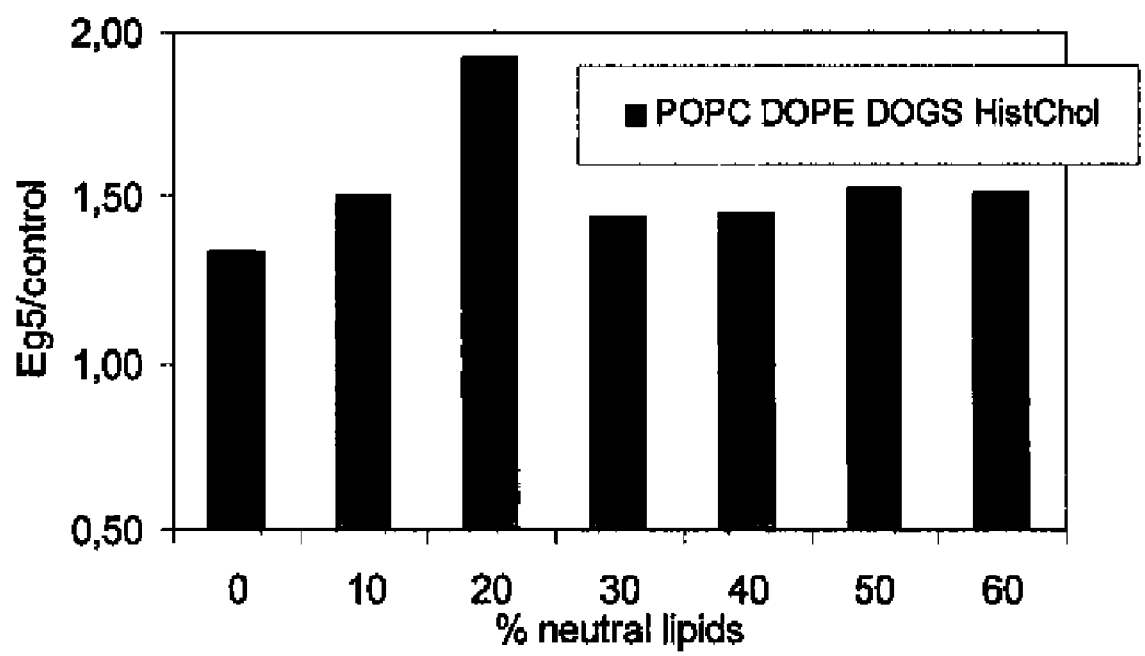
FIG. 4 graphically depicts that in accordance with the invention that mixtures comprising genuine amphoteric lipids likewise benefit from the addition of neutral lipid in terms of functional cell transfection.

Amphoteric liposomes were formulated using the weak anionic lipid dioleoylglycerol hemisuccinate (DOGS) and the amphoteric lipid Hist-Chol at a ratio of about 2:1 with increasing concentrations of a neutral lipid mixture of POPC and DOPE. Maximum transfection efficiency was achieved at about 20% neutral lipids. This experiment further demonstrates, as depicted in FIG. 4, that mixtures comprising genuine amphoteric lipids likewise benefit from the addition of neutral lipid in terms of functional cell transfection.

The principles, preferred embodiments and modes of operation of the presently disclosed have been described in the foregoing specification. The presently disclosed however, is not to be construed as limited to the particular embodiments shown, as these embodiments are regarded as illustrious rather than restrictive. Moreover, variations and changes may be made by those skilled in the art without departing from the spirit and scope of the instant disclosure and disclosed herein and recited in the appended claims.

The invention claimed is:

1. An amphoteric liposome comprising an active ingredient, having an isoelectric point of between 4 and 7, wherein the liposome comprises at least one amphipathic cationic lipid, at least one amphipathic anionic lipid, and at least one neutral lipid, and wherein the liposome is stable at pH 4.2 and Ph 7.5.

2. The amphoteric liposome of claim 1, wherein the liposome has an isoelectric point of between 5 and 7.

3. The amphoteric liposome of claim 1, wherein the neutral lipid is selected from the group consisting of phosphatidyl choline, phosphatidyl ethanolamine, cholesterol, tetraether lipid, ceramide, sphingolipid, and diacyl glycerol.

4. The amphoteric liposome of claim 1 wherein the anionic lipid is a weak anion and the cationic lipid is a strong cation, and the anion is present in excess over the cation.

5. The amphoteric liposome of claim 4, wherein the weak anion is selected from the group consisting of cholesterol hemisuccinate (CHEMS), diacyl glycerol hemisuccinate, fatty acids and phosphatidyl serine.

6. The amphoteric liposome of claim 4, wherein the strong cation is selected from the group consisting of DOTAP, DC-Chol, DORIE, DDAB, TC-Chol, DOTMA, DOGS, $(C18)_2$ $Gly^+N$, N-dioctadecylamido-glycin, CTAB, CpyC and DOEPC.

7. The amphoteric liposome of claim 4, wherein the anionic lipid is CHEMS, diacylglycerol hemisuccinate, or a fatty acid, the cationic lipid is DOTAP or DC-Chol and the neutral lipid is present at 10-60 mol. %.

8. The amphoteric liposome of claim 4, wherein the neutral lipid is present at about 10-20 mol .%.

9. The amphoteric liposome of claim 4, wherein the neutral lipid is cholesterol.

10. The amphoteric liposome of claim 4, wherein the neutral lipid is phosphatidylcholine.

11. The amphoteric liposome of claim 1, wherein the anionic lipid is a weak anion and the cationic lipid is a weak cation.

12. The amphoteric liposome of claim 11, wherein the weak anion is selected from the group consisting of cholesteryl hemisuccinate (CHEMS), diacyl glycerol hemisuccinate, fatty acids and phosphatidyl serine.

13. The amphoteric liposome of claim 11, wherein the weak cation is selected from the group consisting of HisChol and MoChol.

14. The amphoteric liposome of claim 11, wherein the anionic lipid is CHEMS or diacylglycerol hemisuccinate, the cationic lipid is HisChol or MoChol and the neutral lipid is present at 10-60 mol. %.

15. The amphoteric liposome of claim 11, wherein the neutral lipid is present at 10-20 mol. %.

16. The amphoteric liposome of claim 11, wherein the neutral lipid is present at 20-50 mol. %.

17. The amphoteric liposome of claim 11, wherein the neutral lipid is cholesterol.

18. The amphoteric liposome of claim 11, wherein the neutral lipid is phosphatidylcholine.

19. The amphoteric liposome of claim 11, wherein the neutral lipid comprises phosphatidylcholine and phosphatidylethanolamine.

20. The amphoteric liposome of claim 1, wherein the active ingredient is a protein, a peptide, a DNA, and RNA, antisense nucleotide and/or a decoy nucleotide.

21. The amphoteric liposome of claim 1, wherein at least 80 percent of the active ingredient is in the interior of the liposome.

22. The amphoteric liposome of claim 1, wherein the liposome has an average size of between 50 and 1000 nm.

23. The amphoteric liposome of claim 22, wherein the liposome has an average size of between 70 and 250 nm.

24. The amphoteric liposome of claim 22, wherein the liposome has an average size of between 60 and 130 nm.

* * * * *